United States Patent
Kwok et al.

[19]

[11] Patent Number: 6,119,693
[45] Date of Patent: Sep. 19, 2000

[54] FOREHEAD SUPPORT FOR FACIAL MASK

[75] Inventors: Philip Rodney Kwok, West Pymble, Australia; Willedwin John Grant, Rotherhithe, United Kingdom; Robert Stephen Matchett, Mosman, Australia

[73] Assignee: Resmed Limited, North Ryde, Australia

[21] Appl. No.: 09/008,708

[22] Filed: Jan. 16, 1998

[51] Int. Cl.$^7$ .................................................. A62B 18/08
[52] U.S. Cl. ............................... 128/207.11; 128/207.17; 128/207.18; 128/207.13; 128/201.11
[58] Field of Search .......................... 128/207.11, 207.17, 128/207.18, 207.13, 201.22, 201.24, 200.28, 201.18, 201.11; 604/174, 201.26, 201.27

[56] References Cited

U.S. PATENT DOCUMENTS

| | | |
|---|---|---|
| Re. 35,339 | 10/1996 | Rapoport . |
| D. 188,084 | 5/1960 | Garelick . |
| D. 231,803 | 6/1974 | Huddy . |
| D. 250,131 | 10/1978 | Lewis et al. . |
| D. 262,322 | 12/1981 | Mizerak . |
| D. 293,613 | 1/1988 | Wingler . |
| D. 310,431 | 9/1990 | Bellm . |
| D. 323,908 | 2/1992 | Hollister et al. . |

(List continued on next page.)

FOREIGN PATENT DOCUMENTS

| | | |
|---|---|---|
| 91/77110 | 11/1991 | Australia . |
| 94/64816 | 12/1994 | Australia . |
| 95/16178 | 7/1995 | Australia . |
| 32914/95 | 2/1996 | Australia . |
| 9459430 | 2/1996 | Australia . |
| 41018/97 | 4/1998 | Australia . |
| 89312/98 | 1/1999 | Australia . |
| 1039144 | 9/1928 | Canada . |

(List continued on next page.)

OTHER PUBLICATIONS

Mask 1 Photographs, Respironics Inc., Reusable Full Mask (small) Part # 452033 Lot #951108.
Mask 2 Photographs, Puritan—Bennett, Adam Curcuit , Shell Part # 231700 Lot # 616329–00, Pillows (medium) Part #616324.
Mask 3, Photographs, DeVilbiss Healthcare Inc., DeVilbiss Seal–Ring and CPAP Mask Kit (medium), Part 73510–669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510–668.
Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.

*Primary Examiner*—John G. Weiss
*Assistant Examiner*—V. Srivastava
*Attorney, Agent, or Firm*—Pillsbury Madison & Sutro LLP

[57] ABSTRACT

An adjustable forehead support for a nasal mask. The present invention discloses an adjustable forehead support for a nasal or full-face mask wherein the forehead support may be adjusted for the different shapes and sizes of a facial profile. The forehead support utilizes a dual-arm system which adjusts the position of the forehead support vis-à-vis the mask and/or air flow tube. The angle of the mask to the face may be adjusted with the present invention.

46 Claims, 5 Drawing Sheets

U.S. PATENT DOCUMENTS

| | | |
|---|---|---|
| D. 334,633 | 4/1993 | Rudolph . |
| D. 362,061 | 9/1995 | McGinnis et al. . |
| D. 377,089 | 12/1996 | Starr et al. . |
| 781,516 | 1/1905 | Guthrie . |
| 812,706 | 2/1906 | Warbasse . |
| 1,081,745 | 12/1913 | Johnston et al. . |
| 1,192,186 | 7/1916 | Greene . |
| 1,653,572 | 12/1927 | Jackson . |
| 1,926,027 | 9/1933 | Biggs . |
| 2,123,353 | 7/1938 | Catt . |
| 2,248,477 | 7/1941 | Lombard . |
| 2,254,854 | 9/1941 | O'Connell . |
| 2,317,608 | 4/1943 | Heidbrink . |
| 2,371,965 | 3/1945 | Lehmberg . |
| 2,376,871 | 5/1945 | Fink . |
| 2,415,846 | 2/1947 | Randall . |
| 2,438,058 | 3/1948 | Kincheloe . |
| 2,578,621 | 12/1951 | Yant . |
| 2,931,356 | 4/1960 | Schwarz . |
| 2,939,458 | 6/1960 | Lundquist . |
| 3,013,556 | 12/1961 | Galleher . |
| 3,182,659 | 5/1965 | Blount et al. . |
| 3,189,027 | 6/1965 | Bartlett . |
| 3,193,624 | 7/1965 | Webb et al. . |
| 3,238,943 | 3/1966 | Holley . |
| 3,315,674 | 4/1967 | Bloom et al. . |
| 3,330,273 | 7/1967 | Bennett . |
| 3,362,420 | 1/1968 | Blackburn et al. . |
| 3,363,833 | 1/1968 | Laerdal . |
| 3,556,122 | 1/1971 | Laerdal . |
| 3,580,051 | 5/1971 | Blevins . |
| 3,700,000 | 10/1972 | Hesse et al. . |
| 3,720,235 | 3/1973 | Schrock . |
| 3,796,216 | 3/1974 | Schwarz . |
| 3,799,164 | 3/1974 | Rollins . |
| 4,077,404 | 3/1978 | Elam . |
| 4,167,185 | 9/1979 | Lewis . |
| 4,226,234 | 10/1980 | Gunderson . |
| 4,245,632 | 1/1981 | Houston . |
| 4,304,229 | 12/1981 | Curtin . |
| 4,328,797 | 5/1982 | Rollins, III et al. . |
| 4,347,205 | 8/1982 | Stewart . |
| 4,354,488 | 10/1982 | Bartos . |
| 4,402,316 | 9/1983 | Gadberry . |
| 4,412,537 | 11/1983 | Tiger . |
| 4,467,799 | 8/1984 | Steinberg . |
| 4,522,639 | 6/1985 | Ansite et al. . |
| 4,558,710 | 12/1985 | Eichler . |
| 4,616,647 | 10/1986 | McCreadie . |
| 4,622,964 | 11/1986 | Flynn . |
| 4,655,213 | 4/1987 | Rapoport et al. . |
| 4,665,570 | 5/1987 | Davis . |
| 4,671,271 | 6/1987 | Bishop et al. . |
| 4,677,975 | 7/1987 | Edgar et al. . |
| 4,677,977 | 7/1987 | Wilcox . |
| 4,739,755 | 4/1988 | White et al. . |
| 4,770,169 | 9/1988 | Schmoegner et al. . |
| 4,774,941 | 10/1988 | Cook . |
| 4,782,832 | 11/1988 | Trimble et al. . |
| 4,799,477 | 1/1989 | Lewis . |
| 4,809,692 | 3/1989 | Nowacki et al. . |
| 4,819,629 | 4/1989 | Jonson . |
| 4,821,713 | 4/1989 | Bauman . |
| 4,841,953 | 6/1989 | Dodrill . |
| 4,848,334 | 7/1989 | Bellm . |
| 4,848,366 | 7/1989 | Aita et al. . |
| 4,907,584 | 3/1990 | McGinnis . |
| 4,910,806 | 3/1990 | Baker et al. . |
| 4,919,128 | 4/1990 | Kopala et al. . |
| 4,938,210 | 7/1990 | Shene . |
| 4,938,212 | 7/1990 | Gnook et al. . |
| 4,944,310 | 7/1990 | Sullivan . |
| 4,971,051 | 11/1990 | Toffolon . |
| 4,986,269 | 1/1991 | Hakkinen . |
| 4,989,596 | 2/1991 | Macris et al. . |
| 4,989,599 | 2/1991 | Carter . |
| 5,005,568 | 4/1991 | Loescher et al. . |
| 5,005,571 | 4/1991 | Dietz . |
| 5,038,776 | 8/1991 | Harrison et al. . |
| 5,042,473 | 8/1991 | Lewis . |
| 5,042,478 | 8/1991 | Kopala et al. ..................... 128/207.18 |
| 5,046,200 | 9/1991 | Feder . |
| 5,063,922 | 11/1991 | Hakkinen . |
| 5,069,205 | 12/1991 | Urso . |
| 5,109,839 | 5/1992 | Blasdell et al. . |
| 5,109,840 | 5/1992 | Daleiden . |
| 5,121,745 | 6/1992 | Israel . |
| 5,133,347 | 7/1992 | Huennebeck . |
| 5,140,980 | 8/1992 | Haughey et al. . |
| 5,140,982 | 8/1992 | Bauman . |
| 5,159,938 | 11/1992 | Laughlin . |
| 5,178,138 | 1/1993 | Walstrom et al. . |
| 5,231,983 | 8/1993 | Matson et al. . |
| 5,233,978 | 8/1993 | Callaway . |
| 5,243,971 | 9/1993 | Sullivan et al. . |
| 5,265,595 | 11/1993 | Rudolph . |
| 5,279,289 | 1/1994 | Kirk . |
| 5,280,784 | 1/1994 | Kohler . |
| 5,311,862 | 5/1994 | Blasdell et al. . |
| 5,322,057 | 6/1994 | Raabe et al. . |
| 5,343,878 | 9/1994 | Scarberry et al. . |
| 5,357,951 | 10/1994 | Ratner . |
| 5,372,130 | 12/1994 | Stern et al. . |
| 5,388,571 | 2/1995 | Roberts et al. . |
| 5,404,871 | 4/1995 | Goodman et al. . |
| 5,419,318 | 5/1995 | Tayebi . |
| 5,429,126 | 7/1995 | Bracken . |
| 5,429,683 | 7/1995 | Le Mitouard . |
| 5,431,158 | 7/1995 | Tirotta . |
| 5,438,981 | 8/1995 | Starr et al. . |
| 5,441,046 | 8/1995 | Starr et al. . |
| 5,477,852 | 12/1995 | Landis et al. . |
| 5,479,920 | 1/1996 | Piper et al. . |
| 5,488,948 | 2/1996 | Dubruille et al. . |
| 5,492,116 | 2/1996 | Scarberry et al. . |
| 5,501,214 | 3/1996 | Sabo . |
| 5,509,404 | 4/1996 | Lloyd et al. . |
| 5,517,986 | 5/1996 | Starr et al. . |
| 5,538,000 | 7/1996 | Rudolph . |
| 5,540,223 | 7/1996 | Starr et al. . |
| 5,542,128 | 8/1996 | Lomas . |
| 5,546,936 | 8/1996 | Virag et al. . |
| 5,558,090 | 9/1996 | James ................................ 128/207.18 |
| 5,560,354 | 10/1996 | Berthon-Jones et al. . |
| 5,570,682 | 11/1996 | Johnson . |
| 5,570,689 | 11/1996 | Starr et al. . |
| 5,592,938 | 1/1997 | Scarberry et al. . |
| 5,608,647 | 3/1997 | Rubsamen et al. . |
| 5,642,730 | 7/1997 | Baran . |
| 5,647,355 | 7/1997 | Starr et al. . |
| 5,647,357 | 7/1997 | Barnett et al. . |
| 5,649,532 | 7/1997 | Oren . |
| 5,649,533 | 7/1997 | Griffiths . |
| 5,655,520 | 8/1997 | Howe et al. . |
| 5,655,527 | 8/1997 | Scarberry et al. . |
| 5,657,493 | 8/1997 | Ferrero et al. . |
| 5,657,752 | 8/1997 | Landis et al. . |
| 5,662,101 | 9/1997 | Ogden et al. . |
| 5,666,946 | 9/1997 | Langenback . |
| 5,685,296 | 11/1997 | Zdrojkowski et al. . |
| 5,687,715 | 11/1997 | Landis et al. . |
| 5,715,814 | 2/1998 | Ebers . |

| | | | | | | |
|---|---|---|---|---|---|---|
| 5,746,201 | 5/1998 | Kidd . | | 9-216240 | 8/1997 | Japan . |
| 5,813,423 | 9/1998 | Kirchgeorg . | | 1395391 | 5/1975 | United Kingdom . |
| 5,832,918 | 11/1998 | Pantino . | | 1 467 828 | 3/1977 | United Kingdom . |

FOREIGN PATENT DOCUMENTS

| | | | | | | |
|---|---|---|---|---|---|---|
| | | | | 2145335 | 3/1985 | United Kingdom . |
| | | | | 2147506 | 5/1985 | United Kingdom . |
| 0 054 154 | 10/1981 | European Pat. Off. . | | 2 164 569A | 3/1986 | United Kingdom . |
| 0 252 052 A1 | 1/1988 | European Pat. Off. . | | 2 267 648 | 12/1993 | United Kingdom . |
| 0 264 772 A1 | 4/1988 | European Pat. Off. . | | WO 80/01044 | 5/1980 | WIPO . |
| 0 386 605 A1 | 2/1990 | European Pat. Off. . | | WO 82/03548 | 10/1982 | WIPO . |
| 0427474 A2 | 5/1991 | European Pat. Off. . | | WO 86/06969 | 12/1986 | WIPO . |
| 0 462 701 A1 | 12/1991 | European Pat. Off. . | | WO 87/01950 | 4/1987 | WIPO . |
| 0 602 424 | 11/1993 | European Pat. Off. . | | WO 91/03277 | 3/1991 | WIPO . |
| 0 608 684 A1 | 8/1994 | European Pat. Off. . | | WO 92/15353 | 9/1992 | WIPO . |
| 0 697 225 | 7/1995 | European Pat. Off. . | | WO 92/20395 | 11/1992 | WIPO . |
| 178 925 A2 | 4/1996 | European Pat. Off. . | | WO 93/01854 | 2/1993 | WIPO . |
| 0 747 078 A2 | 12/1996 | European Pat. Off. . | | WO 94/02190 | 2/1994 | WIPO . |
| 0 821 978 | 2/1998 | European Pat. Off. . | | WO 94/16759 | 8/1994 | WIPO . |
| 2 574 657 A1 | 6/1986 | France . | | WO 94/20051 | 9/1994 | WIPO . |
| 2 658 725 A1 | 8/1991 | France . | | WO 95/02428 | 1/1995 | WIPO . |
| 2 749 176 | 12/1997 | France . | | WO 96/17643 | 6/1996 | WIPO . |
| 459104 | 4/1928 | Germany . | | WO 96/25983 | 8/1996 | WIPO . |
| 701 690 | 1/1941 | Germany . | | WO 96/39206 | 12/1996 | WIPO . |
| 159396 | 6/1981 | Germany . | | WO 97/07847 | 3/1997 | WIPO . |
| 3015279 A1 | 10/1981 | Germany . | | WO 97/41911 | 11/1997 | WIPO . |
| 3345067 A1 | 6/1984 | Germany . | | WO 98/04310 | 2/1998 | WIPO . |
| 3537507 A1 | 4/1987 | Germany . | | WO 98/11930 | 3/1998 | WIPO . |
| 3539073 A1 | 5/1987 | Germany . | | WO 98/18514 | 5/1998 | WIPO . |
| 4004157 C1 | 4/1991 | Germany . | | WO 98/24499 | 6/1998 | WIPO . |
| 4343205 A1 | 6/1995 | Germany . | | WO 98/26829 | 6/1998 | WIPO . |
| 197 35 359 | 1/1998 | Germany . | | WO 98/26830 | 6/1998 | WIPO . |
| 297 23 101 | 7/1998 | Germany . | | WO 98/48878 | 11/1998 | WIPO . |
| 298 10846 U1 | 8/1998 | Germany . | | | | |

FOREHEAD SUPPORT FOR FACIAL MASK

FIELD OF THE INVENTION

The present invention generally relates to an improved comfort device to be used with a nasal mask. In particular, the device is useful in combination with masks which are used for the treatment of respiratory conditions and assisted respiration. The invention assists in fitting the mask to the face as well.

BACKGROUND OF THE INVENTION

Nasal masks are commonly used in the treatment of respiratory conditions and sleep disorders by delivering a flow of breathable gas to a patient to either assist the patient in respiration or to provide a therapeutic form of gas to the patient to prevent sleep disorders such as obstructive sleep apnea. These nasal masks typically receive a gas through a supply line which delivers gas into a chamber formed by walls of the mask. The mask is generally a semi-rigid mask which has a face portion which encompasses at least the wearer's nostrils. Additionally, the mask may be a full face mask. The mask is normally secured to the wearer's head by straps. The straps are adjusted to pull the mask against the face with sufficient force to achieve a gas tight seal between the mask and the wearer's face. Gas is thus delivered to the mask through the aperture to the wearer's nasal passages and/or mouth.

One of the problems that arises with the use of the mask is that in order for the straps to be tight, the mask is compressed against the wearer's face and may push unduly hard on the wearer's nose. Additionally, the mask may move around vis-à-vis the wearer's face. Thus, there has been provided a forehead support, which provides a support mechanism between the mask and the forehead. This forehead support prevents both the mask from pushing too strongly against the wearer's nose and/or facial region as well as minimize movement of the mask with the addition of a contact point between the mask and the wearer's head as well as minimize uncomfortable pressure points of the mask. Additionally, the forehead support may prevent the air flow tube from contacting the wearer's forehead or face.

Prior to the present invention, the forehead supports were generally a single cushion with a single contact point which may be adjustable by rotation of a screw, with the single cushion pushing on the forehead at a single point. This is oftentimes uncomfortable for the patient, and the adjustability of the distance of the pad for different forehead protuberances oftentimes was difficult if not impossible to be performed. Additionally, a single contact point does not provide necessary lateral support to the mask. Finally, a single contact point may apply too much pressure at the single point.

Examples of prior art nasal masks are shown in U.S. Pat. Nos. 4,782,832 and 5,243,971.

There is a need for an improved forehead support for nasal and facial masks which adjusts to different angles on the face.

There is a need for a forehead support for nasal masks which may be adjusted to different forehead shapes.

There is a need for a multi-point forehead support for nasal masks.

These and other advantages will be described in more detail below.

SUMMARY OF THE INVENTION

The present invention is directed to an improved forehead support for nasal and facial masks. In particular, the present invention utilizes a dual cantilevered forehead support which preferably utilizes dual contacts which are arranged at an obtuse angle with respect to one another and which may be easily adjusted for different forehead protuberances. Preferably, the forehead support has two arms extending from the mask or gas supply line, with the two arms engagable into a bridge system wherein the arms may be adjusted to different positions on the bridge allowing optimal positioning of the mask on the face. This achieves even pressure of the mask on the face. The mask also provides an excellent fit which limits movement of the mask during sleep. The forehead support is adjustable such that the support is closer or further away from the front plane of the facial mask. The bridge supports the pad or pads which contact the wearer's forehead. The support also may allow the mask to be secured such that more pressure is applied to one area of the mask, to seal a leak for example.

The present invention allows the mask user to adjust the angle of the mask to the face. This is possible due to the two point contact of the forehead support to the forehead working in combination with the point of contact of the mask to the face. The system thus has three points of contact, wherein the forehead pads provide two contact points and the mask to the face is a third point of contact. Adjusting the angle of the forehead pads or the distance of the legs to the forehead pads adjusts the angle of the mask vis-à-vis the face of the user. This unique system provides a mask system which can be adjusted to fit the different face angles or profiles required by users.

DETAILED DESCRIPTION OF THE PREFERRED EMBODIMENT

Figure 1:
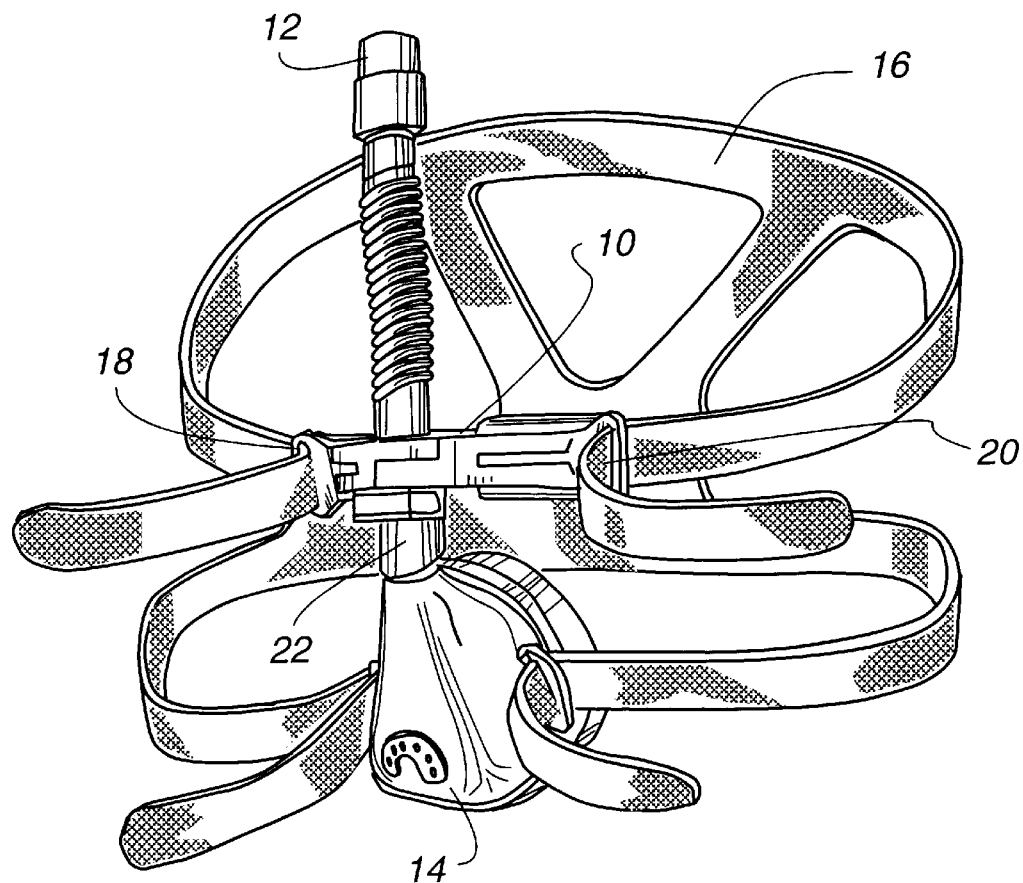
FIG. 1 is a perspective view of the forehead support of the present invention attached to a mask, headgear and a gas supply tube.

FIG. 1 shows a general perspective view of the forehead support 10 of the present invention. The forehead rest or support 10 is attached to an extending airflow tube 12 from the mask 14. The mask 14 and forehead support 10 are shown with headgear 16 which secures the mask 14 to the head of a patient. The headgear 16 may take a variety of forms, with one example being shown as 16. As can be seen in FIG. 1, preferably the headgear 16 loops through the forehead support 10 at 18 and 20. This pulls the forehead support 10 against the forehead, thus creating a snugly fitted mask 14 and also provides a stabilizing member for the mask 14.

The mask 14, shown in FIG. 1 is merely one example of a mask which can be used with a forehead support, but any respiratory mask could be used. A full face mask which may cover the entire face or just both the nose and mouth could be used, for example. Additionally, the airflow tube 12 could be extending from the bottom of the mask 14, thus the tube 12 supporting the forehead support 10 would terminate above forehead support 10. If the airflow tube 12 extended in a downward or other direction from the mask 14, then preferably a post would extend up from the mask 14 (this post position is referenced as 22). This post 22 would terminate slightly above where forehead support 10 is shown secured to tube 12. Thus the forehead support 10 would be secured to the post in this alternative embodiment.

Figure 2:
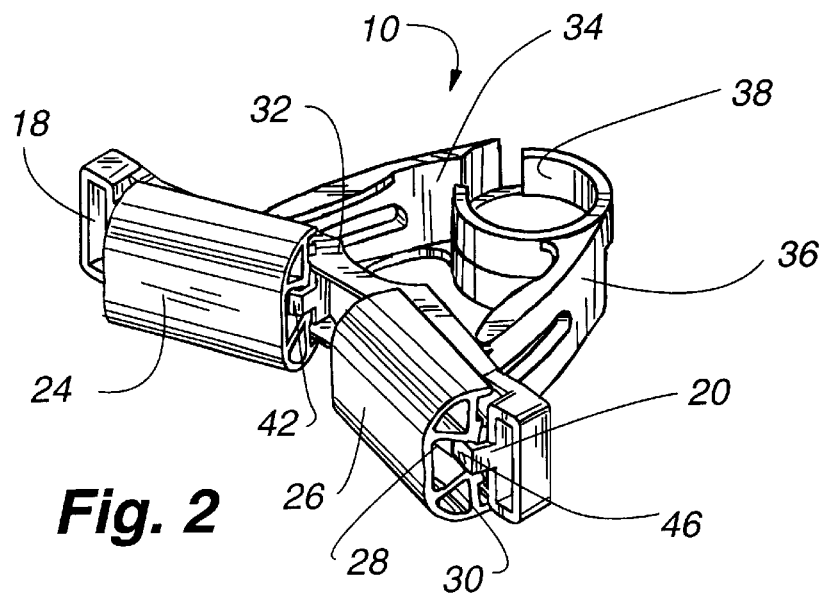
FIG. 2 is a perspective view of the forehead support of the present invention removed from the mask and gas line.

FIG. 2 discloses the preferred construction of the forehead support 10 of the present invention. The forehead support 10 has pads 24 and 26. These pads 24 and 26 are the actual contact points of the forehead support 10 to the forehead. Pads 24 and 26 are preferably made of a deformable elastomeric material which retains its original shape upon release of pressure and provides the wearer with increased comfort and stability. As can be seen in the preferred embodiment, the forehead pads 24 and 26 have an annular interior construction with two retaining walls 28 and 30. The retaining walls 28 and 30 provide structural integrity to the forehead contact support pads yet allow the pads to be deformed. The deformation preferably occurs by deflection of the pad walls. The pads also may be solid pads. The support pads 24 and 26 are mounted to the bridge 32. The bridge 32 provides basically three purposes to the forehead support 10. First off, it acts as a securing means for forehead pads or cushions 24 and 26. Second of all, it has annular spaces 18 and 20 which receive the optional headgear 16 shown in FIG. 1. Finally, it receives arms 34 and 36, which may be adjusted, as described below. The bridge 32 and arms 34 and 36 operate in a cantilever fashion and are preferably made of a polymeric material, which may be easily molded, preferably injection molded. Arms 34 and 36 are secured to bridge 32 by an adjustable locking mechanism which is better illustrated in the figures below. Additionally, arms 34 and 36 join together to create an annular space 38 which may receive airflow tube 12 which is preferably connected to a flow generator to generate breathable air or some type of therapeutic gas. Arms 34 and 36 preferably create an operational hinge. The tube 12 may be an axis of this hinge. The hinge could also be a flexible membrane and not a rotational or axial hinge. Alternatively, the tube may extend through annular space 38 and terminate as described above (in the "post" embodiment) if the air flow tube is connected to another port on the mask.

Figure 3:
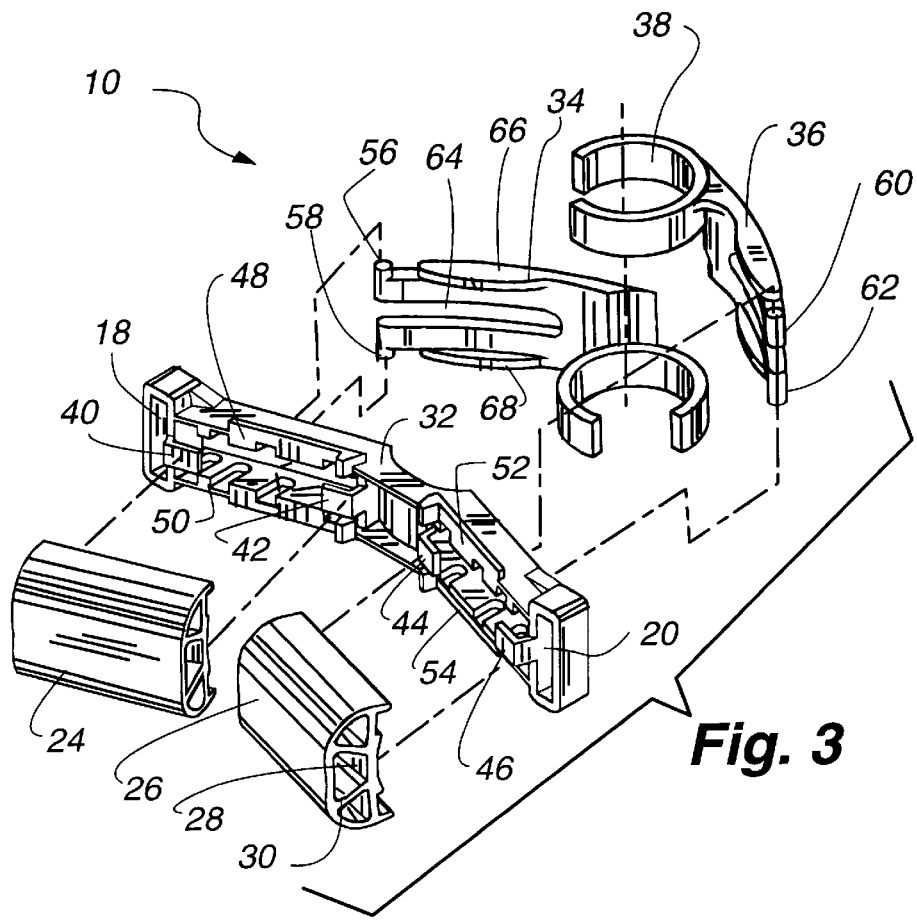
FIG. 3 is an exploded view of the forehead support of the present invention.

FIG. 3 is an exploded view of FIG. 2 and shows the forehead support 10 in greater detail. FIG. 3 discloses how bridge 32 is configured such that forehead pads 24 and 26 may be secured thereto. In particular, tongues 40, 42, 44 and 46 all engage forehead pads 24 and 26 by entering the interior space of the pads. This is shown in FIG. 2 wherein tongues 42 and 46 are shown securing pads 24 and 26 respectively by entering the annular space of the pads 24 and 26. Additionally, there may be engaging surfaces such as 48, 50, 52 and 54, as shown in FIG. 3, which engage an inner side wall of forehead pads 24 and 26. The means by which the forehead pads are secured to the bridge 32 can be done in many manners, and one skilled in the art can come up with numerous methods of achieving this securement. Two sided tape may be used, protruding pegs and apertures on the forehead pad may be used or many other methods. What is desirable is that the forehead pad(s) may be replaced after extended use or, in a clinical setting, with each new patient. The method of securement of the pad(s) to the support is not a limiting feature of the present invention.

The type of forehead pad may also vary, it may include a solid foam sponge, a stuffed pad, a dual durometer foam which may be a single pad or multiple pads attached together, or many other known pads which would impart comfort when placed directly on the forehead. Finally, a single pad which extends all the way across bridge 32 may be used or more than two pads may be used.

Bridge engaging pins 56, 58, 60 and 62 are shown in FIG. 3. As will be more apparent in the figures below, these engaging pins provide for the adjustability of the forehead support 10 of the present invention. There are pin receiving means located on the bridge 32 which receive pins 56, 58, 60 and 62. The pins 56, 58, 60 and 62 are merely one example of how the arms 34 and 36 may be secured to bridge 32. There are other designs which would work just as well as the pin designs. Such designs are known to those skilled in the art. Additionally, there is a space or recess at arms 34 and 36 shown clearly on arm 34 as 64. The purpose of this space 64 is so that the user may compress arm 34 and thus press 56 and 58 together by pressing on surfaces 66 and 68. The purpose of the compression is such that the distance between prongs 56 and 58 is decreased and thereby they may be inserted and locked into bridge 32. The structure and method of this insertion will be described in further detail below.

Figure 4:
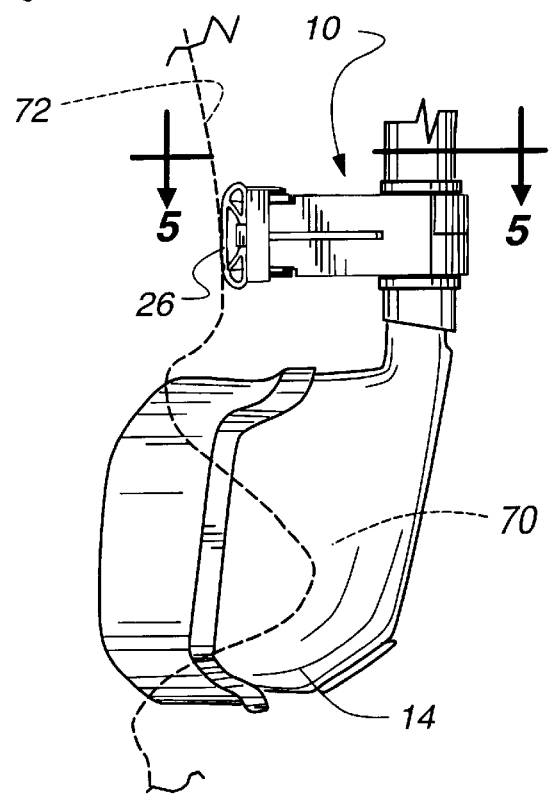
FIG. 4 is a side view of the present invention secured to a mask.

FIG. 4 is a side view of the mask 14 and forehead support 10 of the present invention. The mask is shown as 14 with a dotted line showing the nose of a wearer 70 and the dotted line showing the forehead 72 of the wearer. Pad 26 is shown compressed by the forehead of the individual wearing the mask.

Figure 5:
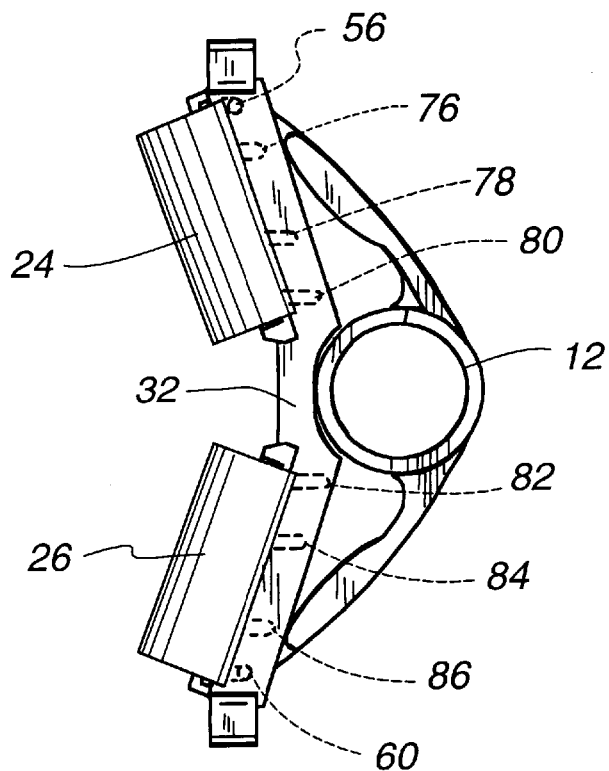
FIG. 5 is a top view of the forehead support of the present invention in a first position.

FIG. 5 is a top view of the forehead support 10 of the present invention taken along lines 5 of FIG. 4. Also, the mask 14 is not shown in FIG. 5. This figure illustrates the forehead support 10 in a position wherein the forehead support is the closest to the tube 12 (shown as merely a space in FIGS. 5–8). The bridge 32 is shown essentially in contact with tube 12. The pins 56, 58, 60 and 62 are shown in their furthest position from the center of the bridge 32. This position may be utilized by someone with a large, protruding or bulbous forehead, or a high nasal bridge, or someone who prefers the airflow tube to be snug against their forehead.

Figure 6:
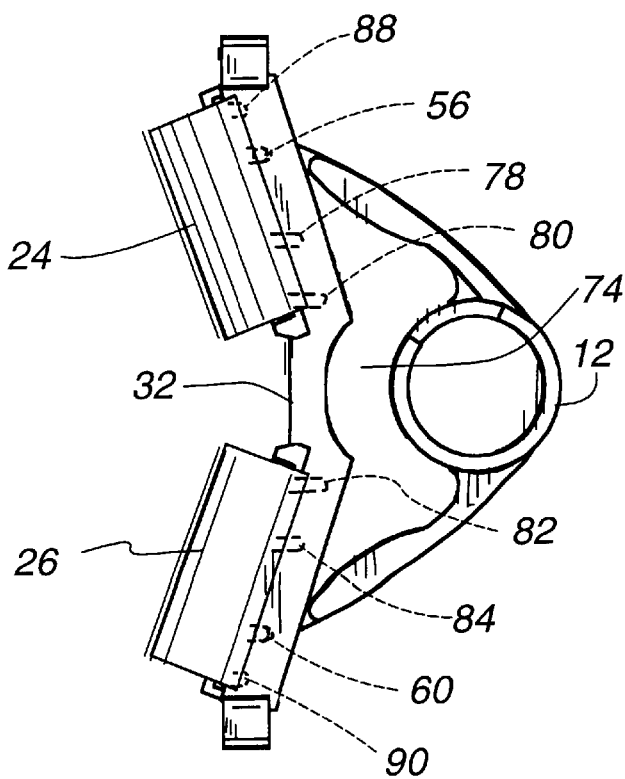
FIG. 6 is a top view of the forehead support of the present invention in a second position.

FIG. 6 shows the same forehead support in the next position, wherein the bridge 32 is moved away from tube 12 such that there is a gap 74 between bridge 32 and tube 12. As is visible from the figure, the forehead support 10 is now moved further away from tube 12, and is positioned differently than in FIG. 5. This may be configured to fit someone with a less protruding forehead, or someone who wants the flexible tube further from their head than is possible in FIG. 5.

Figure 7:
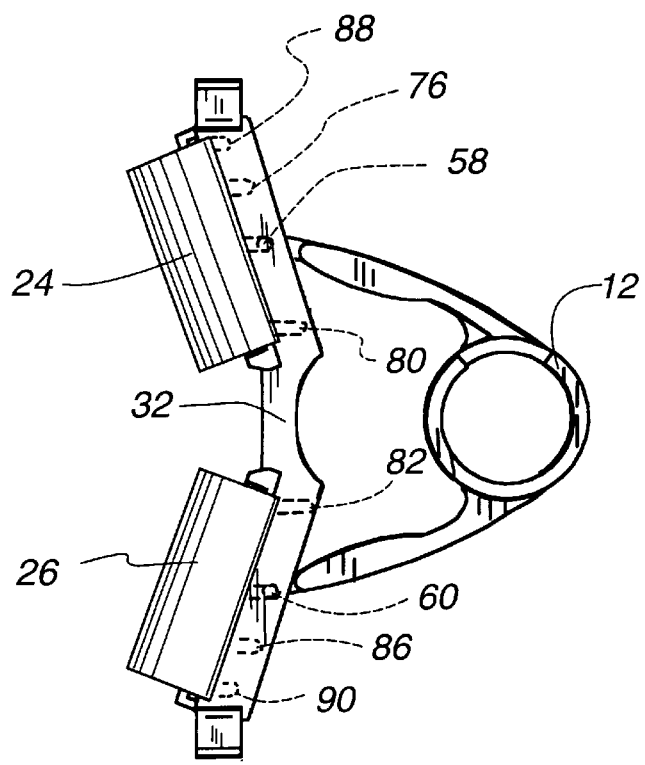
FIG. 7 is a top view of the forehead support of the present invention in a third position.
Figure 8:
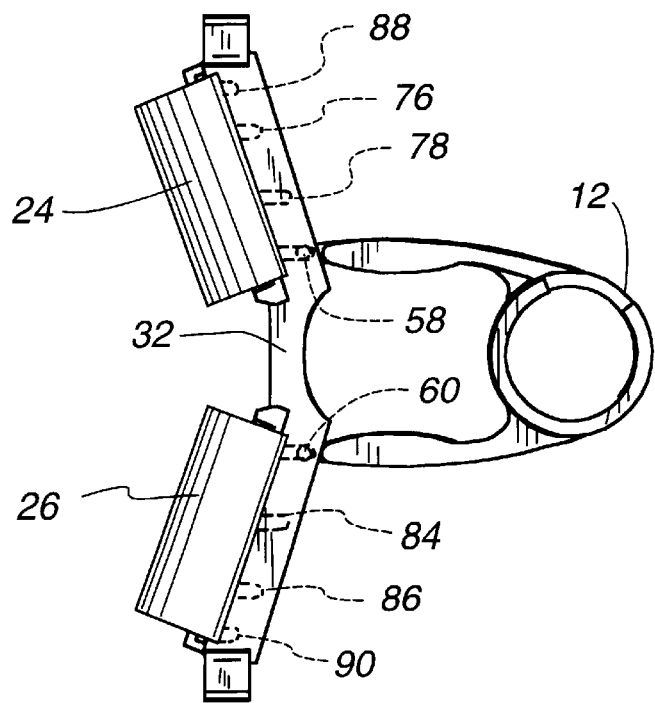
FIG. 8 is a top view of the forehead support of the present invention in a fourth position.

FIGS. 7 and 8 show the third and fourth position for the forehead support of the present invention. Although the present embodiment shows a four-positioned forehead support, the number of slots, shown as 76, 78, 80, 82, 84 86, 88 and 90 may be varied. There may be more or fewer slots, or there may just be one single slot wherein pins 56 and 58 slides transversely across bridge 32 and has locking recesses located along the slide. Additionally, the adjustments do not have to be uniform. In other words, the right side may be adjusted to slot 88 where the left side may be adjusted to slot 84 for some particular patient. There may also be more slots or adjustments on one side of the bridge as compared to the other side of the bridge. Finally, the arms may be coupled such that movement of just one arm moves the other arm in a likewise manner.

Figure 9:
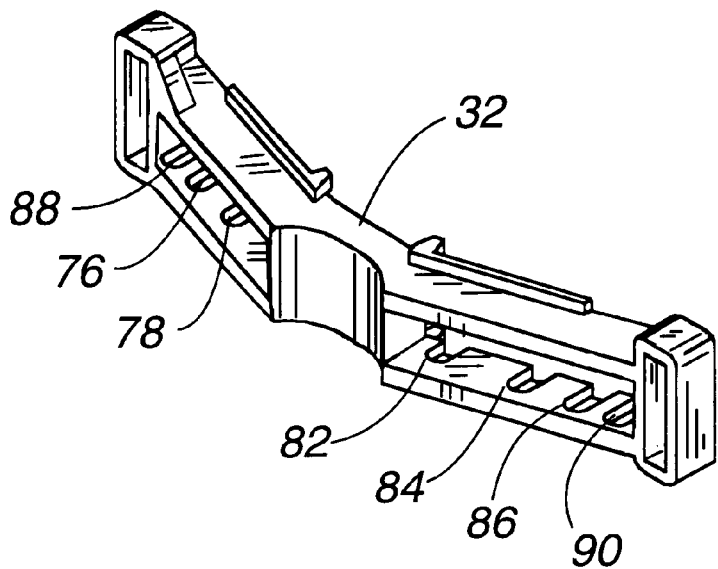
FIG. 9 is a front view of the bridge of the present invention.

FIG. 9 shows an isolated view of bridge 32. The slots 76, 78, 82, 84, 86, 88 and 90 are visible from this view. The slots are configured such that prongs 56, 58, 60 and 62 may be inserted therein. There is a mirror set of slots on the upper portion of bridge 12 which are not visible in FIG. 9. Again, there can be additional slots, fewer slots, or different methods of locking the arms 34 and 36 to various positions along the bridge 32. What is important to the present invention is that the bridge 32 with the accompanying pads 24 and 26 may be positioned to a variety of distances between the tube 12 and the pads 24 and 26. Additionally, the pad may be one continuous pad, three pads, five pads, four pads, etc. There also may a double bridge used, wherein there could be a total of two or more pads with two bridges.

Figure 10:
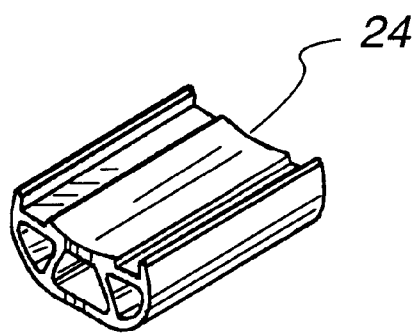
FIG. 10 is a single pad of the present invention.

FIG. 10 is a perspective view of the preferred forehead pad of the present invention. As indicated above, there could be many shapes or variations of a forehead pad and type of forehead pad or the shape of forehead pad is not limited in the present invention.

It is to be understood that while the invention has been described above in conjunction with preferred specific embodiments, the description and examples are intended to illustrate and not limit the scope of the invention, which is defined by the scope of the appended claims.

What is claimed:

1. A forehead support for a respiratory mask having an extension, said forehead support adapted to be secured to the extension of the respiratory mask, said forehead support comprising:
    a bridge, said bridge being adapted to receive at least one forehead pad, said bridge having a first and second securing means and a first and second end;
    an arm, said arm securing said bridge to said extension of said mask, said arm having a first and second end, said first end having a first attaching means which is adapted to secure to said first securing means in a first position to said first end of said bridge, said second end of said arm having a second attaching means which is adapted to secure to said second securing means in a first position to said second end of said bridge;
    said first securing means having at least two positions which may receive said first attaching means; and
    said second securing means having at least two positions which may receive said second attaching means.

2. The forehead support of claim 1 wherein said first and second attaching means comprises at least two pins at the terminal end of said first and second arms.

3. The forehead support of claim 2 wherein said first and second securing means use a plurality of slots to receive said pins.

4. The forehead support of claim 1 wherein said arm is a two-piece structure.

5. The forehead support of claim 2 wherein each of said arms has a space extending transversely a partial length of said arms.

6. The forehead support of claim 1 wherein there are two pads.

7. The forehead support of claim 1 wherein said first and second securing means is a slot extending across said bridge.

8. The forehead support of claim 1 wherein said extension is an airflow tube.

9. The forehead support of claim 1 wherein said mask is a full face mask.

10. The forehead support of claim 1 wherein said mask is adapted to treat a sleeping disorder.

11. The forehead support of claim 1 wherein the first and second securing means are different means.

12. The forehead support of claim 1 wherein the arms wrap tightly around an airflow tube which extends into said mask.

13. The forehead support of claim 1 wherein said extension is on said mask.

14. The forehead support of claim 1 wherein adjusting said arm adjusts the angle the mask makes vis-à-vis the user's face.

15. A respiratory mask to be worn by a patient, said mask having an airflow tube entering said mask and a forehead support secured to the airflow tube, said forehead support comprising:
    at least two forehead pads;
    a bridge, said bridge being adapted to receive the at least two forehead pads at an obtuse angle, said bridge having a plurality of pin receiving slots at a first and second bridge end, said pin receiving slots defining a first and second position at each first and second bridge end; and
    first and second arms, said arms securing said bridge to said airflow tube, said arms having a first and second end, said first arm end having a pair of engageable pins adapted to secure said first arm in said first and second positions relative to said first end of said bridge, said second end of said second arm having a pair of engageable pins adapted to secure said second arm in said first and second positions relative to said second end of said bridge.

16. The forehead support of claim 15 wherein each of said arms has a space extending transversely a partial length of said arms.

17. The forehead support of claim 15 wherein there are two pads.

18. The forehead support of claim 15 wherein said mask is a full face mask.

19. The forehead support of claim 15 wherein said mask is adapted to treat a sleeping disorder.

20. A forehead support constructed and arranged to be connected to and support a respiratory mask, comprising:
    a bridge constructed and arranged to engage a forehead of a user, the bridge having a first side and a second side, the bridge also having a plurality of first adjusting points spaced along the first side and a plurality of second adjusting points spaced along the second side;
    a first arm having a bridge end and a mask end, the first arm bridge end having an engagement mechanism constructed and arranged for selectively engaging each of the plurality of first adjusting points, the first arm mask end constructed and arranged for connecting to a first connecting portion connected to the mask; and
    a second arm having a bridge end and a mask end, the second arm bridge end having an engagement mechanism constructed and arranged for selectively engaging each of the plurality of second adjusting points, the second arm mask end constructed and arranged for connecting to a second connecting portion connected to the mask;
    wherein, selective movement of the first arm bridge engagement mechanism between the plurality of first adjusting points alters a spacing distance between the first side of the bridge and the first connecting portion and selective movement of the second arm bridge engagement mechanism between the plurality of second adjusting points alters a spacing distance between the second side of the bridge and the second connecting portion.

21. The forehead support of claim 20, wherein:

the first arm bridge end engagement mechanism comprises a pair of extending portions separated by a space, the extending portions constructed and arranged to be selectively movable relative to one another between an expanded position where the extending portions are separated by the space and a compressed position where the separating space is reduced, at least one of the extending portions comprising a projecting pin; and each of the plurality of first adjusting points comprises a slot constructed and arranged for selective engagement with the first arm projecting pin when the first arm extending portions are in the expanded position, and for selective disengagement with the first arm projecting pin when the first arm extending portions are in the compressed position.

22. The forehead support of claim 21, wherein:

the second arm bridge end engagement mechanism comprises a pair of extending portions separated by a space, the extending portions constructed and arranged to be selectively movable relative to one another between an expanded position where the extending portions are separated by the space and a compressed position where the separating space is reduced, at least one of the extending portions comprising a projecting pin; and each of the plurality of second adjusting points comprises a slot constructed and arranged for selective engagement with the second arm projecting pin when the second arm extending portions are in the expanded position, and for selective disengagement with the second arm projecting pin when the second arm extending portions are in the compressed position.

23. The forehead support of claim 22, wherein each of the plurality of first and second adjusting points comprises a pair of slots and each of the first and second arm extending portions comprises a projecting pin constructed and arranged for selective engagement and disengagement with one of the pair of slots, respectively.

24. The forehead support of claim 23, and further comprising the respiratory mask, the respiratory mask comprising an airflow tube, the first and second connecting portions being positioned on the airflow tube.

25. The forehead support of claim 24, wherein each of the first and second arm mask ends is pivotally connected about an axis of the airflow tube.

26. The forehead support of claim 25, and further comprising:

a first cushion pad connected to the first side of the bridge and constructed and arranged to be positioned between the bridge and the forehead of the user; and a second cushion pad connected to the second side of the bridge and constructed and arranged to be positioned between the bridge and the forehead of the user.

27. The forehead support of claim 20, and further comprising the respiratory mask, the respiratory mask comprising an airflow tube, the first and second connecting portions being positioned on the airflow tube.

28. The forehead support of claim 27, wherein each of the first and second arm mask ends is pivotally connected about an axis of the airflow tube.

29. The forehead support of claim 28, and further comprising:

a first cushion pad connected to the first side of the bridge and constructed and arranged to be positioned between the bridge and the forehead of the user; and a second cushion pad connected to the second side of the bridge and constructed and arranged to be positioned between the bridge and the forehead of the user.

30. The forehead support of claim 20, and further comprising the respiratory mask.

31. A forehead support constructed and arranged to be connected to and support a respiratory mask, comprising:

a bridge constructed and arranged to engage a forehead of a user, the bridge having a first side and a second side;

a first arm having a bridge end and a mask end, the first arm bridge end having an engagement mechanism constructed and arranged for selectively engaging the bridge within a first adjustment range between a first position and a second position along the first side of the bridge, the first arm mask end constructed and arranged for pivotable connection about an axis of an airflow tube connected to the mask; and a second arm having a bridge end and a mask end, the second arm bridge end having an engagement mechanism constructed and arranged for selectively engaging the bridge within a second adjustment range between a third position and a fourth position along the second side of the bridge, the second arm mask end constructed and arranged for pivotable connection about the axis of the airflow tube;

wherein, selective pivotable movement of the first arm about the axis of the airflow tube varies the position of engagement of the first arm and the bridge within the first adjustment range, thereby altering a spacing distance between the first side of the bridge and the airflow tube, and selective pivotable movement of the second arm about the axis of the airflow tube varies the position of engagement of the second arm and the bridge within the second adjustment range, thereby altering a spacing distance between the second side of the bridge and the airflow tube.

32. The forehead support of claim 31, wherein:

the bridge first adjustment range comprises a plurality of spaced apart first adjusting points; and the first arm bridge end engagement mechanism is constructed and arranged for selectively en gaging each of the plurality of first adjusting points as the first arm is pivoted about the axis of the airflow tube.

33. The forehead support of claim 32, wherein:

the bridge second adjustment range comprises a plurality of spaced apart second adjusting points; and the second arm bridge end engagement mechanism is constructed and arranged for selectively engaging each of the plurality of second adjusting points as the second arm is pivoted about the axis of the airflow tube.

34. The forehead support of claim 33, wherein:

the first arm bridge end engagement mechanism comprises a pair of extending portions separated by a space, the extending portions constructed and arranged to be selectively movable relative to one another between an expanded position where the extending portions are separated by the space and a compressed position where the separating space is reduced, at least one of the extending portions comprising a projecting pin; and each of the plurality of first adjusting points comprises a slot constructed and arranged for selective engagement with the first arm projecting pin when the first arm extending portions are in the expanded position, and for selective disengagement with the first arm projecting pin when the first arm extending portions are in the compressed position.

35. The forehead support of claim 34, wherein:

the second arm bridge end engagement mechanism comprises a pair of extending portions separated by a space, the extending portions constructed and arranged to be selectively movable relative to one another between an expanded position where the extending portions are separated by the space and a compressed position where the separating space is reduced, at least one of the extending portions comprising a projecting pin; and each of the plurality of second adjusting points comprises a slot constructed and arranged for selective engagement with the second arm projecting pin when the second arm extending portions are in the expanded position, and for selective disengagement with the second arm projecting pin when the second arm extending portions are in the compressed position.

36. The forehead support of claim 35, wherein each of the plurality of first and second adjusting points comprises a pair of slots and each of the first and second arm extending portions comprises a projecting pin constructed and arranged for selective engagement and disengagement with one of the pair of slots, respectively.

37. The forehead support of claim 36, and further comprising the respiratory mask.

38. The forehead support of claim 31, and further comprising:

a first cushion pad connected to the first side of the bridge and constructed and arranged to be positioned between the bridge and the forehead of the user; and a second cushion pad connected to the second side of the bridge and constructed and arranged to be positioned between the bridge and the forehead of the user.

39. The forehead support of claim 31, and further comprising the respiratory mask.

40. The forehead support of claim 39, and further comprising:

a first cushion pad connected to the first side of the bridge and constructed and arranged to be positioned between the bridge and the forehead of the user; and a second cushion pad connected to the second side of the bridge and constructed and arranged to be positioned between the bridge and the forehead of the user.

41. An adjustable support constructed and arranged to be connected to and support a device attached to a user's body, comprising:

a bridge constructed and arranged to engage the user's body, the bridge having a first side and a second side, the bridge also having a plurality of first adjusting points spaced along the first side and a plurality of second adjusting points spaced along the second side;

a first arm having a bridge end and a support end, the first arm bridge end having an engagement mechanism constructed and arranged for selectively engaging each of the plurality of first adjusting points; and a second arm having a bridge end and a support end, the second arm bridge end having an engagement mechanism constructed and arranged for selectively engaging each of the plurality of second adjusting points, the first arm support end being movably connected to the second arm support end at a connecting portion;

wherein, selective movement of the first arm bridge engagement mechanism between the plurality of first adjusting points alters a spacing distance between the first side of the bridge and the connecting portion and selective movement of the second arm bridge engagement mechanism between the plurality of second adjusting points alters a spacing distance between the second side of the bridge and the connecting portion.

42. The adjustable support of claim 41, wherein:

the first arm bridge end engagement mechanism comprises a pair of extending portions separated by a space, the extending portions constructed and arranged to be selectively movable relative to one another between an expanded position where the extending portions are separated by the space and a compressed position where the separating space is reduced, at least one of the extending portions comprising a projecting pin; and each of the plurality of first adjusting points comprises a slot constructed and arranged for selective engagement with the first arm projecting pin when the first arm extending portions are in the expanded position, and for selective disengagement with the first arm projecting pin when the first arm extending portions are in the compressed position.

43. The adjustable support of claim 42, wherein:

the second arm bridge end engagement mechanism comprises a pair of extending portions separated by a space, the extending portions constructed and arranged to be selectively movable relative to one another between an expanded position where the extending portions are separated by the space and a compressed position where the separating space is reduced, at least one of the extending portions comprising a projecting pin; and each of the plurality of second adjusting points comprises a slot constructed and arranged for selective engagement with the second arm projecting pin when the second arm extending portions are in the expanded position, and for selective disengagement with the second arm projecting pin when the second arm extending portions are in the compressed position.

44. The adjustable support of claim 43, wherein each of the plurality of first and second adjusting points comprises a pair of slots and each of the first and second arm extending portions comprises a projecting pin constructed and arranged for selective engagement and disengagement with one of the pair of slots, respectively.

45. The adjustable support of claim 44, and further comprising:

a first cushion pad connected to the first side of the bridge and constructed and arranged to be positioned between the bridge and the body of the user; and a second cushion pad connected to the second side of the bridge and constructed and arranged to be positioned between the bridge and the body of the user.

46. A respiratory mask assembly, comprising:

a respiratory mask;

a headgear connected to the respiratory mask for attaching the mask to a user's head; and a forehead support constructed and arranged to be connected to and support the respiratory mask, comprising:

a bridge constructed and arranged to engage a forehead of the user, the bridge having a first side and a second side, the bridge also having a first plurality of opposed pairs of adjusting slots spaced along the first side and a second plurality of opposed pairs of adjusting slots spaced along the second side;

a first arm having a bridge end and a mask end, the first arm bridge end comprising a pair of extending portions separated by a space, the extending portions constructed and arranged to be selectively movable relative to one another between an expanded position where the extending portions are separated by the space and a compressed position where the separating space is reduced, each of the extending portions comprising a projecting pin, the pair of projecting pins constructed and arranged for selective engagement with each of the first plurality of opposed pairs of adjusting slots when the extending portions are in the expanded position and for selective disengagement with such opposed pair of adjusting slots when the extending portions are in the compressed position, the first arm mask end pivotally connected about an air tube connected to the respiratory mask; and a second arm having a bridge end and a mask end, the second arm bridge end comprising a pair of extending portions separated by a space, the extending portions constructed and arranged to be selectively movable relative to one another between an expanded position where the extending portions are separated by the space and a compressed position where the separating space is reduced, each of the extending portions comprising a projecting pin, the pair of projecting pins constructed and arranged for selective engagement with each of the second plurality of opposed pairs of adjusting slots when the extending portions are in the expanded position and for selective disengagement with such opposed pair of adjusting slots when the extending portions are in the compressed position, the second arm mask end pivotally connected about the air tube connected to the respiratory mask;

wherein, selective movement of the first arm bridge end between the first plurality of opposed pairs of adjusting slots alters a spacing distance between the first side of the bridge and the air tube and selective movement of the second arm bridge end between the second plurality of opposed pairs of adjusting slots alters a spacing distance between the second side of the bridge and the air tube.

* * * * *